US005891657A

United States Patent [19]

Itak et al.

[11] Patent Number: 5,891,657
[45] Date of Patent: Apr. 6, 1999

[54] IMMUNOASSAY STANDARDS FOR VOLATILE ANALYTES WITH BENZENE RINGS

[75] Inventors: Jeanne A. Itak, Hamilton, N.J.; Michele Y. Selisker, Churchville; David P. Herzog, Warrington, both of Pa.

[73] Assignee: Strategic Diagnostics Inc., Newark, Del.

[21] Appl. No.: 246,216

[22] Filed: May 19, 1994

[51] Int. Cl.$^6$ .................................................. G01N 33/553
[52] U.S. Cl. .............................. 435/7.93; 436/8; 436/526; 436/815
[58] Field of Search ........................... 435/7.93; 436/526, 436/815

[56] References Cited

U.S. PATENT DOCUMENTS

| | | | |
|---|---|---|---|
| 4,208,399 | 6/1980 | Karol et al. | 424/1 |
| 4,241,177 | 12/1980 | Singh et al. | 435/7 |
| 4,383,984 | 5/1983 | Karol et al. | 424/1 |
| 4,456,691 | 6/1984 | Stark | 436/543 |
| 4,489,157 | 12/1984 | Khanna et al. | 435/7 |
| 4,503,143 | 3/1985 | Gerber et al. | 435/7 |
| 4,594,327 | 6/1986 | Zuk | 436/514 |
| 4,596,771 | 6/1986 | Cidlowski et al. | 435/7 |
| 4,650,771 | 3/1987 | Buckler et al. | 436/536 |
| 4,900,664 | 2/1990 | Israel et al. | 435/7 |
| 5,273,909 | 12/1993 | Piasio | 436/518 |
| 5,358,851 | 10/1994 | Peck | 435/7.93 |
| 5,384,262 | 1/1995 | Piasio et al. | 436/518 |
| 5,411,869 | 5/1995 | Itak et al. | 435/7.93 |
| 5,449,611 | 9/1995 | Friedman et al. | 435/7.93 |

FOREIGN PATENT DOCUMENTS 9412536  6/1994  WIPO ........................... C07K 13/00

OTHER PUBLICATIONS

D Tech Published 1993, EM Science/Strategic Diagnostics Inc. "BTEX Test Kit Instruction Guide," TK–1003–1.
Millipore, "EnviroGard™ Petroleum Hydrocarbons Test Kit," Rev. 1993, pp.2–10.
International Search Report, PCT application PCT/US95/06207.
PETRO RIS® Soil Test System, PETRO RIS® Water Test System, 1992 Rev. 1.
Allen et al., Published 1992, Journal of Soil Contamination, "A Rapid and Sensitive Immunoassay for the Detection of Gasoline and Diesel Fuel in Contaminated Soil," pp.227–237.
Rittenburg et al., Reprinted from Soils magazine Oct. 1992, Quantix Portable Workstation, "Test in the fast lane".
Quantix, 1992, Portable Workstation User Guide, pp. 1–31.
Potter et al., (1993), The Eighth Annual Contaminated Soils Conference, "Analysis of Petroleum Contaminated Soil and Water" , pp.2–80.
Kostecki et al., (Allen et al.), (1992), Lewis Publishers, Inc., "Development of a Monoclonal Antibody Immunoassay for the Detection of Gasoline and Diesel Fuel in the Environment," pp. 37–46.
James Fleeker, (1987), J. Association of Official Analytical Chemists, "Two Enzyme Immunoassays to Screen for 2,4–Dichlorophenoxyacetic Acid in Water," pp. 874–878.
Lawruk et al., Bull. Environ. Contam. Toxicol. (1994), "Quantification of 2,4–D and Related Chlorophenoxy Herbicides by a Magnetic Particle–Based ELISA," pp. 538–545.
M. Gomes et al., "Immunological Methods for the Detection of Benzo[a] pyrene Metabolites in Urine," Chem. Res. Toxicol., pp. 307–310 (1990).

*Primary Examiner*—Mary E. Ceperley
*Attorney, Agent, or Firm*—Volpe and Koenig, P.C.

[57] ABSTRACT

An immunoassay directed at certain analytes that have benzene rings, such that the immunoreactive standard used is less volatile than the analyte, and kits for performing the assay.

17 Claims, 8 Drawing Sheets

IMMUNOASSAY STANDARDS FOR VOLATILE ANALYTES WITH BENZENE RINGS

FIELD OF THE INVENTION

The invention relates to improvements in immunoassays for volatile analytes whose structure comprises a benzene ring.

BACKGROUND

The identification of the petroleum contaminants in soil or of oil sheens on water is very important for identifying the source and extent of the contamination. Those contaminants include a wide variety of volatile organic contaminants (VOC's) such as benzene, toluene, ethylbenzene, and xylenes. However, analysis of those compounds is difficult because VOC's are rapidly volatilized; loss can amount to three orders of magnitude during sampling, transportation, storage, and analytical processes. (T. Potter and J. Bruya (1993) *Analysis of Petroleum Contaminated Soil and Water*, from the 8th Annual Soils Conference, Univ. Mass.).

A separate problem arises because of the need for a standard in many immunoassays used to determine the concentration of the VOC. Ideally, the response (e.g., amount of color in an ELISA method) generated due to addition of the sample with an unknown analyte concentration is compared to the response generated when a known amount of analyte (the standard) is added. VOC's in aqueous solution, however, are not good standards because their concentration changes with time due to evaporation.

In view of the foregoing, it would be highly desirable to (1) be able to perform on-site analysis in order to minimize loss of such volatile compounds by minimizing transportation and storage of the samples, and (2) be able to use non-volatile standards for calibrating the assay in order to avoid loss of the standards during transportation from their site of manufacture to the site of testing.

On-site analysis is not possible for methods such as chromatography but it is possible for immunoassay analysis. Commercially available immunoassay test kits usually use either the VOC's themselves or a petroleum product mix, such as home heating oil, as calibrators. The disadvantage of the VOC's is their volatility; the disadvantage of the petroleum product mix is that it is a highly heterogeneous mixture, with batch-to-batch variations in its composition and therefore its immunoreactivity. Additionally, even the petroleum mixes contain VOC's that will evaporate and result in a decrease of immunoreactivity with time.

BRIEF SUMMARY OF THE INVENTION

An immunoassay directed at certain analytes that have benzene rings, such that the immunoreactive standard used is less volatile than the analyte.

DESCRIPTION OF THE INVENTION

In a general aspect, the invention is an immunoassay for an analyte, said immunoassay a process that comprises the steps of:

1) reacting a sample with an antibody preparation, said sample comprising an amount of analyte, said antibody reactive against said analyte, 2) reacting a known amount of standard with an antibody preparation of the same specificity as that used in step (1), it being required that the standard be immunoreactive with the antibody preparation, 3) calculating the amount or an upper limit to the amount of analyte present in the sample used in step (1), wherein the analyte has a boiling point less than 200° C. and comprises a benzene ring such that said benzene ring may be part of a multi-ring structure (such as naphthalene), wherein said benzene ring may be substituted at one or more of its six carbon atoms, and wherein the substituent at one atom need not be the same as the substituent at another atom (although it is preferred that the substituents be the same), wherein not more then one substituent on said benzene ring is other than I, Cl, Br, OH, —$CH_3$, or —$NO_2$, wherein any substituent on said benzene ring that is not I, Cl, Br, OH, —$CH_3$, or —$NO_2$, has a backbone chain that does not have more than six atoms, wherein the standard is a compound that displays at least 70 per cent nonvolatilization in water (preferably with tris, BSA, Proclin, and EDTA as in Example 4) after 14 day storage at 25° C. (or in range, 15°–30° C.) when stored in a closed 3 ml vial as a 2 ml aqueous solution.

When used in the immunoassays of this invention, the standard need not be stored as a 2 ml solution in a 3 ml vial; those storage conditions are merely the ones used to determine whether the standard has the desired stability for the immunoassay.

Fourteen days is an Environmental Protection Agency (EPA)-recommended maximum storage time for samples.

In a particular embodiment, the immunoassay comprises the steps of:

1) reacting a sample with an antibody preparation, said sample comprising an amount of analyte, said antibody reactive against said analyte, 2) reacting a known amount of standard with an antibody preparation of the same specificity as that used in step (1), 3) quantitating the amount of the antibody preparation that reacted with the sample in step (1), 4) quantitating the amount of antibody preparation that reacted with the standard in step (2), 5) utilizing the amounts quantitated in steps (3) and (4) and the known amount in step (2) to calculate the amount or an upper limit to the amount of analyte present in the sample used in step (1).

Preferred standards are compounds that have (1) a molecular weight greater than 130 and/or (2) more than ten atoms, each selected from the group, C, N, and O. For compounds with characteristics (1) and/or (2), particularly preferred are standards that comprise a benzene ring (but optionally may have more than one ring structure). Also particularly preferred are compounds that comprise both a benzene ring and a methyl group substituent on that benzene ring. Where there is a methyl group substituent, benzene ring substituents with long chains (more than 6 atoms) are preferably in a meta position relative to that methyl group.

N-(3-methylbenzyl)-diglycolic acid, monoamide, has eight atoms in its backbone chain: in the direction away from the benzene ring, the atoms are C, N, C, C, O, C, C, C, and O. Monovalent atoms such as H or halogens are not considered part of the backbone chain.

In a particular embodiment, the immunoassay of the invention comprises reacting an antibody preparation with the analyte, said antibody preparation prepared by using an immunogen that comprises xylene linked via one of its methyl groups to a carrier (such as a protein). In a preferred embodiment, the immunogen comprises m-xylene linked via one of its methyl groups to a carrier.

In another embodiment of the invention, the immunoassay is one wherein the analyte has a boiling point of less than 200° C.

Preferably the analyte is selected from the group:

m-xylene, p-xylene, o-xylene, ethylbenzene, toluene, benzene, naphthalene, 1,2,4-trimethylbenzene, styrene, creosote, 1,3,5-tri-methylbenzene, and n-propylbenzene.

The immunoassay is particularly useful when the analyte is part of a mixture selected from the group, gasoline, diesel fuel, jet fuel (especially, Jet-A fuel), and kerosene.

In a preferred embodiment of the invention, the immunoassay is one wherein the standard is a substantially pure preparation of a single compound. However, the standard may, for example, be a mixture of one or more substantially pure compounds, said mixture constructed by mixing together portions of substantially pure preparation of said compounds.

A substantially pure preparation of a compound is one in which substantially all of the compounds have the same structure. A pure preparation is therefore different from home heating oil or other mixture of compounds.

The analyte is the compound being tested for.

A variety of substances will be seen to be capable of generating a color or other response in the immunoassay. Therefore, if the nature of the analyte in the sample is unknown, then for each possible analyte one can only assign an upper limit to the concentration of that analyte. For many purposes, however, such information is sufficient to determine the extent and degree of contamination, to delineate pollutant plumes in ground water, to monitor well placement, and for preliminary identification and quantitation of pollutants.

A highly preferred standard is N-(3-methylbenzyl)-diglycolic acid, monoamide.

The immunoassays to which the present invention is applicable include: (1) Competition assays (as used in the Examples) where the analyte competes with labeled (enzyme-analyte analog) conjugate for binding sites provided by an antibody and detection is accomplished by measuring the decrease in the amount of labeled conjugate bound to the antibodies; (2) non-competition assays, where the analyte does not compete for such binding sites and the antibody is labelled with a detectable label; (3) sandwich assays, where one anti-analyte antibody acts as a bridge to bind the analyte to a solid phase, and detection is accomplished with a detectably-labelled second anti-analyte antibody that is allowed to attach the solid phase-bound analyte; or (4) any other immunoassay format. Indeed the term "immunoassay" is intended here in a very general sense and is any assay in which an antibody specific for an analyte of interest is used. Nevertheless, for the smallest analytes, sandwich assays may be difficult because of the need for two antibody binding sites.

The antibodies may be polyclonal or monoclonal. The use of hybridomas to create monoclonal antibodies is well known in the art. The fact that polyclonal antibodies against a compound can be created is an indicator that a monoclonal antibody against that compound can be created.

Detectable labels include fluorescent, radioactive, and chemiluminescent labels. The labels may be linked directly to other molecules of interest, such as antibodies, or indirectly by streptavidin-biotin linkages or other linkages. The labels may be bound directly to the antibodies or conjugates, or alternatively, be generated from substrates by enzymes attached to antibodies or substrates.

PREPARATION OF N-(3-METHYLBENZYL)-DIGLYCOLIC ACID, MONOAMIDE

N-(3-methylbenzyl)-diglycolic acid, monoamide was prepared as follows: 2.4 g (0.02 moles) of 3-methylbenzylamine (Aldrich Chemical) was added to 3.0 g (0.026 mole) of diglycolic anhydride (Aldrich) dissolved in 15 mL dioxane. The solution was warmed, with stirring, at 70°–80° C. for 60 min. After cooling slightly, water was added to near the cloud point. After standing 60 minutes at room temperature, the crystals were filtered by suction, washed with water, and air dried. Recrystallized from water-ethanol.

PREPARATION OF THE ANTIBODIES USED IN THE EXAMPLE, INCLUDING PREPARATION AND STRUCTURE OF THE IMMUNOGEN

The structure of the immunogen is as follows:

The immunogen is prepared by dissolving 0.6 mmole of 3-methylphenylacetic acid in 10 ml dry p-dioxane. The solution is treated with 0.6 mmole of triethylamine in 2.4 mL of the same solvent. The solution is cooled and 0.6 mmole of isobutylchloroformate in 2.4 mL dioxane is added. The solution is swirled and allowed to stand 30 to 40 minutes at ca. 20° C. to form the mixed anhydride of the ligand. (A precipitate of triethylamine hydrochloride forms which is not removed.) The carrier protein (300 mg of hemocyanin, serum albumin or other appropriate carrier) is dissolved in 50 ml of 0.2M sodium borate, pH 8.7, and the resulting solution is diluted with 20 ml of dioxane. The protein solution is cooled in ice-water. With cooling and constant stirring, the mixed anhydride is added dropwise to the carrier protein over a 10–15 min period. The reaction solution is stirred and cooled another 45 minutes, then the solution is removed from the bath and allowed to strand at room temperature for 45–60 minutes.

If necessary, the conjugate preparation is filtered through densely packed glass wool in the apex of a funnel, or through Whatman No. 2 paper. The solution is dialyzed at 4° C. against 0.1M sodium borate, pH 8.7 (1×8 L), and water (2×8 L), in that order. The dialyzed immunogen solution is freeze-dried.

Assay of the immunogen solution with picrylsulfonic acid indicates that 39–48% of the amino groups are blocked. (Snyder, S. L. and P. Z. Sobocinsid, (1975) An improved 2,4,6-trinitrobenzenesulfonic acid method for the determination of amines, *Anl. Biochem.* 64:284–88).

The immunogen was injected into rabbits and the antibodies were prepared as follows: The immunogen was dissolved or suspended in sterile saline to a concentration of 4 mg/ml. It was mixed with an equal amount of Freund's adjuvant and then emulsified. On Day 1, a total of 0.5 ml of the emulsion is injected into the hip muscle of the rabbit and a control bleed is done. On Day 20, the back of the animal is shaved and, in 6–8 sites, inject a total of 0.5 ml of emulsion. On Day 30, a test bleed is done. On day 45, the immunization of Day 20 is repeated. On Day 55, a test bleed is done.

The immunization described for Day 20 is repeated at 30-day intervals using Freund's complete adjuvant. The interval is lengthened if antibody production is inadequate or the animal is distressed.

The animal is bled 7–10 days after immunization (30–50 ml).

PREPARATION OF THE ENZYME CONJUGATE 0.250 g of N-(3-methylbenzyl)diglycolic acid, monoamide was dissolved with 0.125 g of N'-hydroxysuccinimide (NHS) in 25 ml dry ethyl acetate. A solution of 0.250 g N'-dicyclohexylcarbodiimide (DCC) was dissolved in 5 ml dry ethyl acetate is added to the NHS/ligand solution with stirring at 4° C. The solution was stirred overnight and allowed to come to room temperature. The preparation was centrifuged to remove precipitate. The ethyl acetate was evaporated with nitrogen, and the ester was redissolved in 2 mL of dimethylformamide (DMF).

2 mL of ester solution in DMF is added to a solution of 44 mg of horse radish peroxidase (HRP) in 0.5 m carbonate buffer and was allowed to stir overnight at room temperature. The solution was centrifuged again to remove precipitate and chromatographed on a Sephadex G-25 colum to isolate the HRP fraction.

PREPARATION OF THE ANTIBODY-LINKED MAGNETIC PARTICLES

Attachment of the antibodies to magnetic particles was done as follows: One mL of a 50 mg/ml suspension of BioMag 4100 amine-terminated particles (Advanced Magnetics, Cambridge, Mass.) was activated with 5% (v/v) glutaraldehyde in 2 mL of 0.01M MES buffer, pH 6 (MES is 2-N-morpholine)ethanesulfonic Acid) for 3 hours. Unreacted glutaraldehyde was removed by washing four times with 5 ml of 0.01M MES buffer. Rabbit anti-serum containing the antibodies was diluted to an antibody concentration of 5 mg/mL and 1 mL was reacted with the activated magnetic particles by shaking for 16 hours. A 1M glycine solution was then used to quench any unreacted sites for 30 minutes. The particles were washed four times with 5 ml of Tris buffered saline with 0.1% bovine serum albumin (BSA), pH 7.4 and diluted in the same buffer to achieve an iron concentration of 8–10 mg/ml.

ASSAY PROCEDURE USED IN THE EXAMPLES

The sample to be tested is added, along with the enzyme conjugate, to a disposable test tube followed by the addition of paramagnetic particles with analyte-specific antibodies attached. At the end of an incubation period, a magnetic field is applied to hold the paramagnetic particles (with analyte and enzyme-conjugate bound to the antibodies on the particles, in proportion to their original concentration in the tube) in the tube and allow the unbound reagents to be decanted. After decanting, the particles are washed with Washing Solution.

The presence of analyte is detected by adding the enzyme substrate (hydrogen peroxide) and the chromogen (3,3',5,5'-tetramethylbenzidine). The enzyme-conjugate bound to the anti-analyte antibody catalyzes the conversion of the substrate/chromogen mixture to a colored product. After an incubation period, the reaction is stopped and stabilized by the addition of acid. Since the conjugate was in competition with the unlabeled analyte for the antibody sites, the color developed is inversely proportional to the concentration of analyte in the sample.

The anti-analyte antibody is a rabbit antibody covalently bound to paramagnetic particles, which are suspended in 150 mM Tris, 150 mM NaCl, 1 mM EDTA, 0.1% BSA, with 15 ppm active Proclin, pH 7.4.

The enzyme-conjugate is in 25 mM Tris, 150 mM NaCl, 4 mM DNS, 0.1 mM Luminol, 0.1% BSA with 15 ppm active Proclin (manufactured by Rohm and Haas, purchased from Supelco), 0.005% hemoglobin, pH 6.0.

The standards, calibrated to have an immunoreactivity equivalent to specific Total BTEX concentrations, are in 25 mM Tris, 150 mM NaCl, 1 mM EDTA, 0.1% BSA, with 15 ppm active Proclin, pH 7.4.

The Control, calibrated to have an immunoreactivity equivalent to a concentration of approximately 2.1 ppm Total BTEX, is in 25 mM Tris, 150 mM NaCl, 1 mM EDTA, 0.1% BSA, with 15 ppm active Proclin, pH 7.4. The Control sample can be used to determine whether an assay is providing the correct value for analyte concentration.

The Diluent/Zero Standard is 25 mM Tris, 150 mM NaCl, 1 mM EDTA, 0.1% BSA, with 15 ppm active Proclin, pH 7.4 but without detectable analyte.

The Color Solution used in the Examples was made of equal parts of two components (1) 3,3',5,5'-tetramethylbenzidine (TMB) (0.4 g/ml) in 26% dimethylformamide and (2) 0.02% hydrogen peroxide in citric buffer pH 4.5. A one component system (TMB 1-component Membrane Substrate) can be obtained from Kirkegaard and Perry Laboratories (Gaithersburg, Md.).

The Stopping Solution is a solution of sulfuric acid (0.5%).

The Washing Solution is deionized water with 0.1% Proclin 150.

Test tubes are polystyrene tubes.

Reagents are stored at 2°–8° C., not frozen.

Precision pipets capable of delivering 200 and 500 µl, and a 1.0 ml repeating pipet are used. The Vortex Mixer is a Thermolyne Maxi Mix, Scientific Industries Vortex Genie, or equivalent. The photometer is capable of readings at 450 nm.

The sample to be tested for analyte concentration is water or diluted soil extract. Water samples are collected according to EPA guidelines in glass screw cap VOA vials with teflon-faced silicone septum and stored cool (4° C.). Care is taken that during sample collection to minimize agitation that would drive off volatile compound. Vials are completely filled as much as possible, to eliminate as much free air space as possible. Soil samples may be analyzed by extracting them with calcium chloride in 75% methanol and then diluting them in tris-buffered saline containing preservatives and stabilizers.

Samples containing gross particulate matter are filtered (e.g.,m with 02 $\mu$m Acrodisc® PTFE, Gelman Science) to remove particles.

"Total BTEX" contains equivalent concentrations of benzene, toluene, ethylbenzene, and m-, o-, and p-xylene (i.e., 1 ppm of Total BTEX contains 1 ppm each of benzene, toluene, ethylbenzene, and m-, o-, and p-xylene).

If the analyte concentration of a sample exceeds 3 ppm of Total BTEX or its immunoreactive equivalent, the sample is subject to repeat testing using a diluted sample. Prior to assay, a ten-fold or greater dilution of the sample is recommended with an appropriate amount of Diluent/Zero Standard and mixing thoroughly.

The following substances up to 2500 ppm were found to have no significant effect on the assay: phosphates, magnesium, nickel, and nitrate. The following substances were found to have no significant effect up to 1000 ppm: calcium, copper, sulfate, thiosulfate, and zinc. The following substances were found to have no effect up to 500 ppm: iron, humic acid, manganese, mercury, and sulfite. Sodium chloride up to 0.5M showed no significant effect on the assay.

All reagents must be allowed to come to room temperature and the antibody-coupled paramagnetic particles are mixed thoroughly just prior to pipetting into the assay.

To minimize loss of volatile compounds, the sample, conjugate and particle addition steps are performed in as timely a fashion as possible.

Reagents are added directly to the bottom of the tube while avoiding contact between the reagents and the pipet tip. This helps assure consistent quantities of reagent in the test mixture.

To avoid cross-contamination and carryover of reagents by using clean pipets for each sample and by avoiding contact between reagent droplets on the tubes and pipet tips.

Foam formation is avoided during vortexing.

The magnetic separation rack consists of two parts: an upper rack which will securely hold the test tubes and a lower separator which contains the magnets used to attract the antibody coupled paramagnetic particles. During incubations, the upper rack is removed from the lower separator so that the paramagnetic particles remain suspended during the incubation. For separation steps, the rack and the separator are combined to pull the paramagnetic particles to the sides of the tubes.

The rack is decanted by inverting it away from the operator using a smooth turning action so that the liquid flows consistently along only one side of the test tube. While still inverted, the rack is placed on an absorbent pad and allowed to drain. The rack is lifted replaced gently onto the pad several times to insure complete removal of the liquid from the rim of the tube.

The total time required for pipetting the magnetic particles are kept to one minute or less.

The assay is done as follows:
1. 200 $\mu$l of either standard, control or sample is added to each tube.
2. 250 $\mu$l of conjugate is added to each tube.
3. The antibody-coupled paramagnetic particles are mixed thoroughly and 500 ul of them are added to each tube (The stock solution with a concentration of 8–10 mg iron/ml was diluted 1:1000 in 150 mM Tris, 150 mM NaCl, 1 mM EDTA, 0.1% BSA with 15 ppm Proclin, pH 7.4 and 500 ul was added to each tube).
4. Tubes are vortexed for 1 to 2 seconds minimizing foaming.
5. Tubes are incubated for 15 min at room temperature (15°–30° C.).
6. Tubes in the magnetic rack are placed over a magnetic base for two minutes.
7. The tubes are decanted and gently blotted briefly in a consistent manner.
8. One ml of Washing Solution is added to each tube and the tubes are allowed to remain in the separation rack for two minutes.
9. Decant and gently blot all tubes briefly in a consistent manner.
10. Repeat steps 8 and 9 an additional time.
11. Remove the rack from the separator and add 500 $\mu$l of Color Solution to eac tube.
12. Vortex for 1 to 2 seconds minimizing foaming.
13. Incubate for 20 minutes at room temperature.
14. Add 500 $\mu$l of Stopping Solution to each tube.
15. Read results at 450 nm within 15 minutes after adding the Stopping Solution.

The results are calculated by:
1. Calculating the mean absorbance value for each standard.
2. Calculating the % $B/B_0$ for each standard by dividing the mean absorbance value for the standard by the mean absorbance value for the Diluent/Zero Standard In other words if the mean absorbance value for the standard is 0.5 times the mean absorbance value for the Diluent/Zero Standard then the % $B/B_0$ is 50% and the concentration of standard used is the 50% $B/B_0$ concentration.)
3. Constructing a standard curve by plotting the % $B/B_0$ for each standard on vertical logit (Y) axis versus the corresponding analyte concentration on a horizontal algorithmic (X) axis.
4. % $B/B_0$ for controls and sample will then yield levels in ppm of analyte by interpolation using the standard curve.

Data can, if desired, be analyzed by a commercially available data storer and analyzer, such as the Ohmicron RaPID Analyzer available from Ohmicron, Newtown, Pa. 18940. Such automated analyzers are used to make direct optical readings and use a microprocessor to convert optical readings to sample concentrations by comparing the results to those obtained with calibration curves.

EXAMPLES

Example 1

Results with various volatile compounds as standards

Toluene, propyl benzene, o-xylene, p-xylene, and m-xylene (all at 10 ppm) and benzene (100 ppm) were tested for their value as standards. They were stored in 10 ml of distilled water at room temperature (15°–30° C.) in an open test tube (18 mm in diameter, and 150 mm in length).

Figure 1:
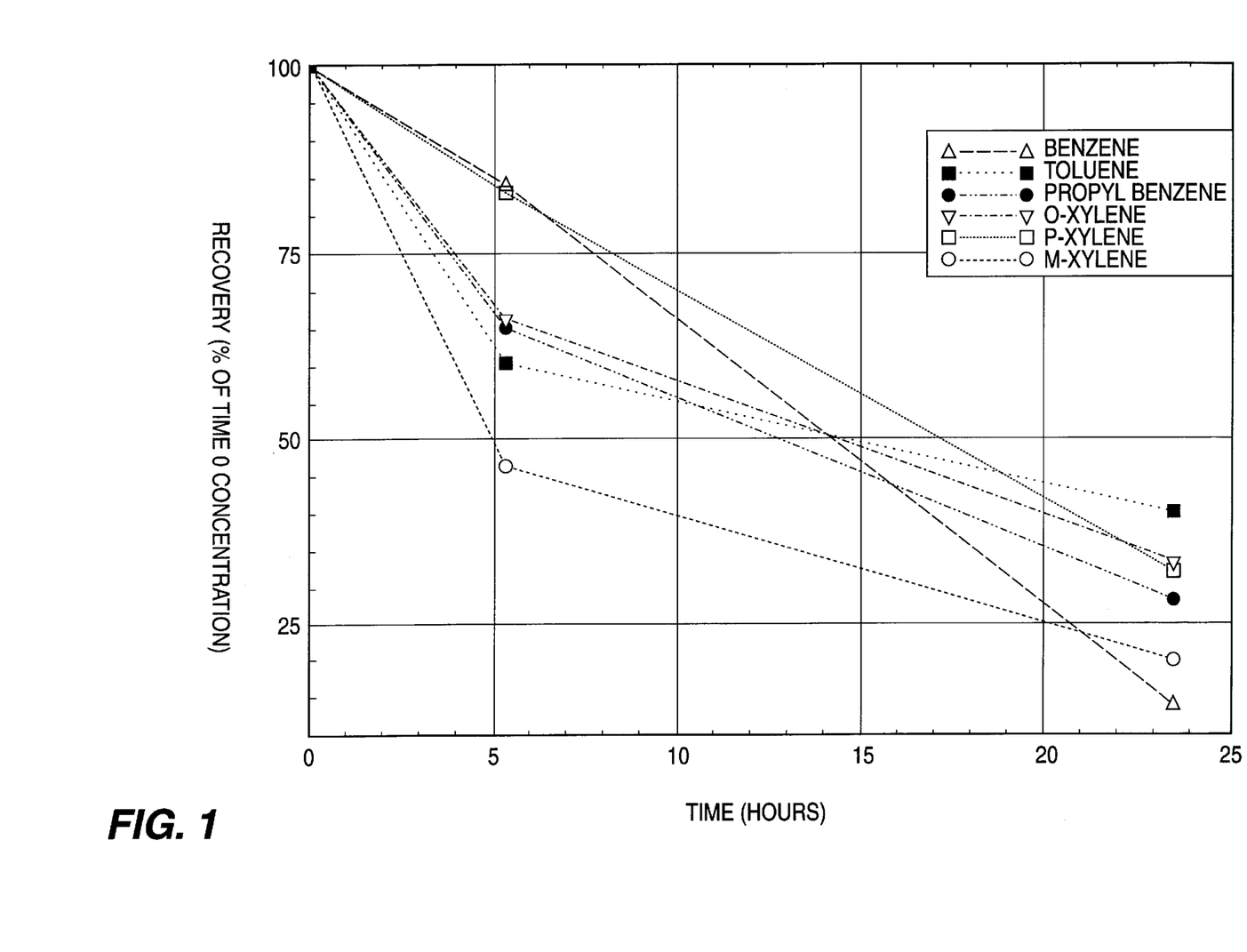
FIG. 1 Shows the loss of a volatile compound upon storage, as indicated by an immunoassay.

The results are shown in FIG. 1. The "Recovery" was taken to be inversely proportional to the light at 450 nm generated in the assay. The results show the decrease in immunoreactivity reactivity of the compounds as a function of time of incubation and indicate that none of them are good standards. The loss of reactivity as a function of time was concluded that the loss was due to volatilization and not chemical decomposition of the compounds. Also the loss was so great that it was concluded that even if the solutions had been incubated as 2 ml aliquots in 3 ml closed vials, much more than 30 percent would have volatilized over a 14-day period.

Example 2

Analysis of well-water samples was done using N-(3-methylbenzyl)-diglycolic acid, monoamide as the standard at concentrations of 0.035 ppm, 0.10 ppm. and 0.75 ppm which are equivalent to 0.09, 0.35, and 3.00 ppm Total BTEX, respectively.

The well water was spiked with Total BTEX. The results are shown in Table 1.

TABLE 1

Assay Results

| BTEX added in ppm | Mean (ppm) | S.D. (ppm) | % of amount added |
| --- | --- | --- | --- |
| 0.15 | 0.13 | 0.02 | 88 |
| 0.50 | 0.52 | 0.07 | 105 |
| 1.00 | 1.12 | 0.13 | 111 |
| 1.50 | 1.67 | 0.19 | 111 |
|  |  | Average: | 104 |

Example 3

The cross-reactivity, of the antibodies used in the assay, for various petroleum hydrocarbons was tested and the results expressed as least detectable dose (LDD) which is estimated as the dose needed to generate a $B/B_0$ of 90%. (B equals 0.9 times $B_0$). The results are shown in Table 2. The concentration in ppm needed to generate a $B/B_0$ of 50% is also shown in Table 2.

TABLE 2

| Compound | LDD (ppm) | 50% $B/B_0$ |
| --- | --- | --- |
| Total BTEX | 0.02* | 0.65* |
| m-xylene | 0.03 | 1.80 |
| p-xylene | 0.13 | 3.10 |
| o-xylene | 0.22 | 4.70 |
| ethylbenzene | 0.24 | 7.80 |
| toluene | 0.44 | 7.40 |
| benzene | 0.59 | 51.0 |
| naphthalene | 0.03 | 0.59 |
| 1,2,4-trimethylbenzene | 0.04 | 1.15 |
| anthracene | 0.06 | 28.0 |
| styrene | 0.07 | 2.60 |
| hexachlorobenzene | 0.08 | NR |
| phenanthrene | 0.08 | 1.60 |
| creosote | 0.10 | 4.76 |
| 1,3,5-tri-methylbenzene | 0.14 | 3.50 |
| acenaphthene | 0.17 | 6.20 |
| n-propylbenzene | 0.27 | 4.70 |
| n-hexane | 2.35 | NR |
| n-octane | 3.40 | NR |
| n-nonane | 4.40 | NR |
| n-heptane | 6.30 | 72 |
| cyclohexane | 8.30 | NR |
| n-decane | 13.5 | NR |
| methylene chloride | NR | NR |
| trichloroethylene | NR | NR |
| regular gasoline | 0.54 | 9.02 |

TABLE 2-continued

| Compound | LDD (ppm) | 50% $B/B_0$ |
| --- | --- | --- |
| premium gasoline | 0.75 | 7.20 |
| mineral spirits | 1.12 | 24.9 |
| diesel | 1.29 | 16.2 |
| kerosene | 1.50 | 24.0 |
| Jet-A-Fuel | 2.70 | 33.5 |
| Household lubricant | 15.8 | NR |

*note that 0.02 ppm for Total BTEX means 0.02 ppm of each of the six components of Total BTEX. Similarly 0.65 is the concentration of each component of Total BTEX needed so that Total BTEX will generate a 50% $B/B_0$.

NR means a compound was nonreactive up to 100 ppm.

Example 4

The stability (lack of volatilization) of a solution of N-(3-methylbenzyl)diglycolic acid, monoamide dissolved in 2 ml of 25 mM Tris, 150 mM NaCl, 1 mM EDTA, 0.1% BSA, and 15 mM active Proclin, pH 7.4, was tested as a function of storage time. Storage was effected by incubating the 2 ml of solution in a stoppered vial with a 3 ml capacity. The one ml of open "head space" in the vial was sufficient to allow volatilization of the N-(3-methylbenzyl)-diglycolic acid, monoamide.

Figure 2:
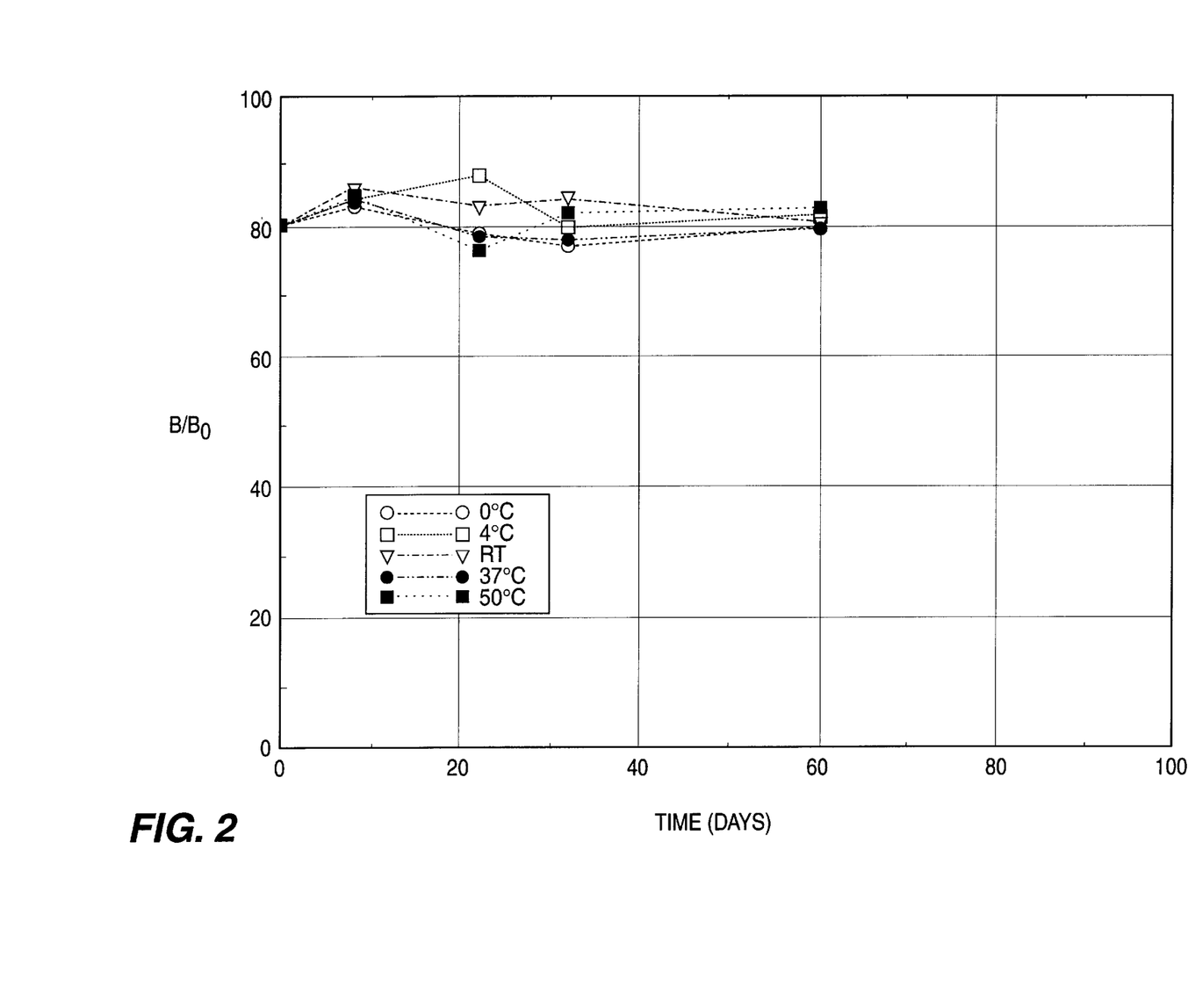
FIGS. 2, 3, and 4 show the lack of loss of N-(3-methylbenzyl)-diglycolic acid, monoamide, as a function of storage time.

In FIG. 2, the concentration of N-(3-methylbenzyl)-diglycolic acid, monoamide was 0.035 ppm, which is equivalent to approximately 0.09 ppm Total BTEX.

Figure 3:
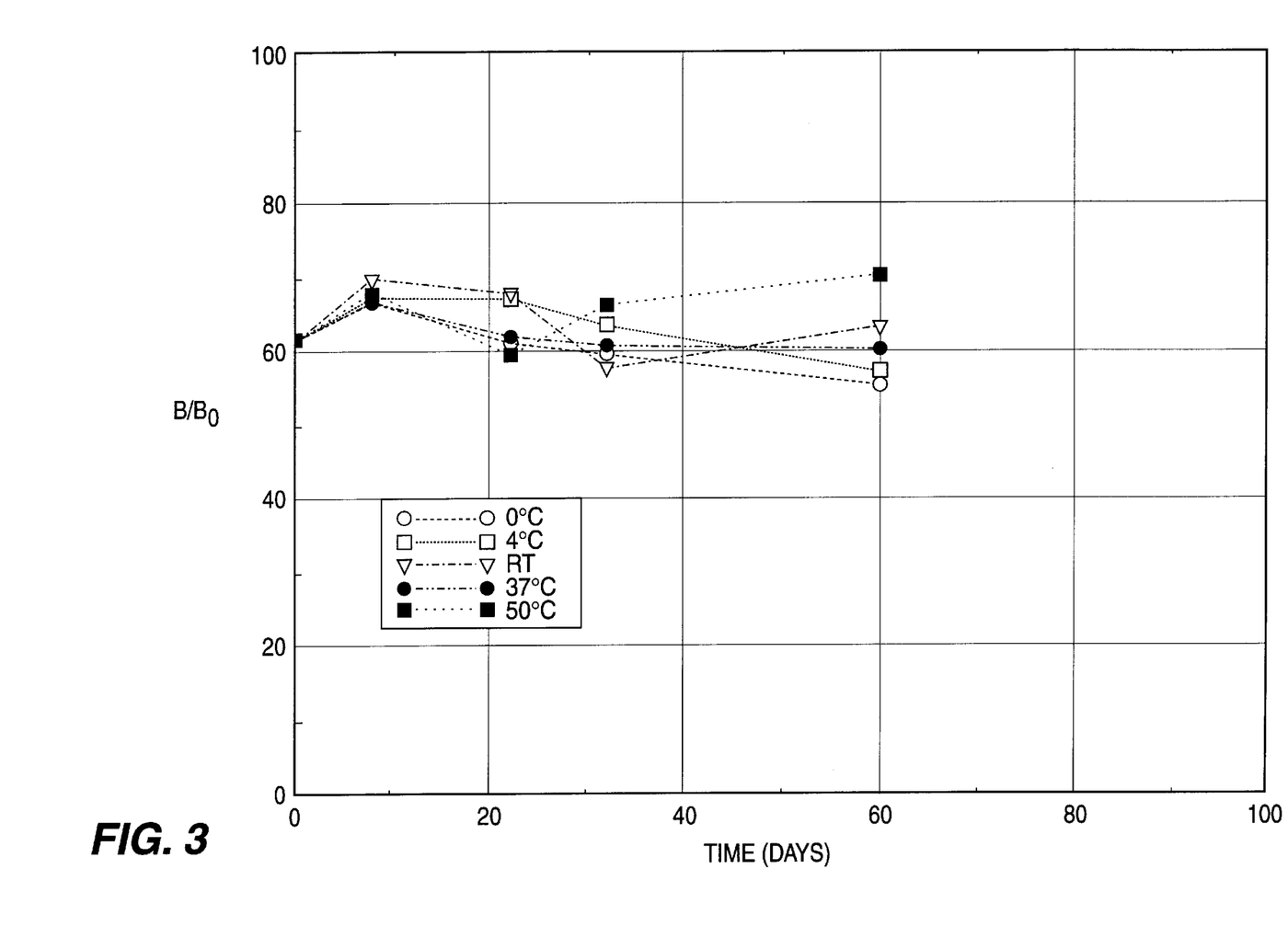

In FIG. 3, the concentration of N-(3-methylbenzyl)-diglycolic acid, monoamide was 0.10 ppm which is equivalent to approximately 0.35 ppm Total BTEX.

Figure 4:
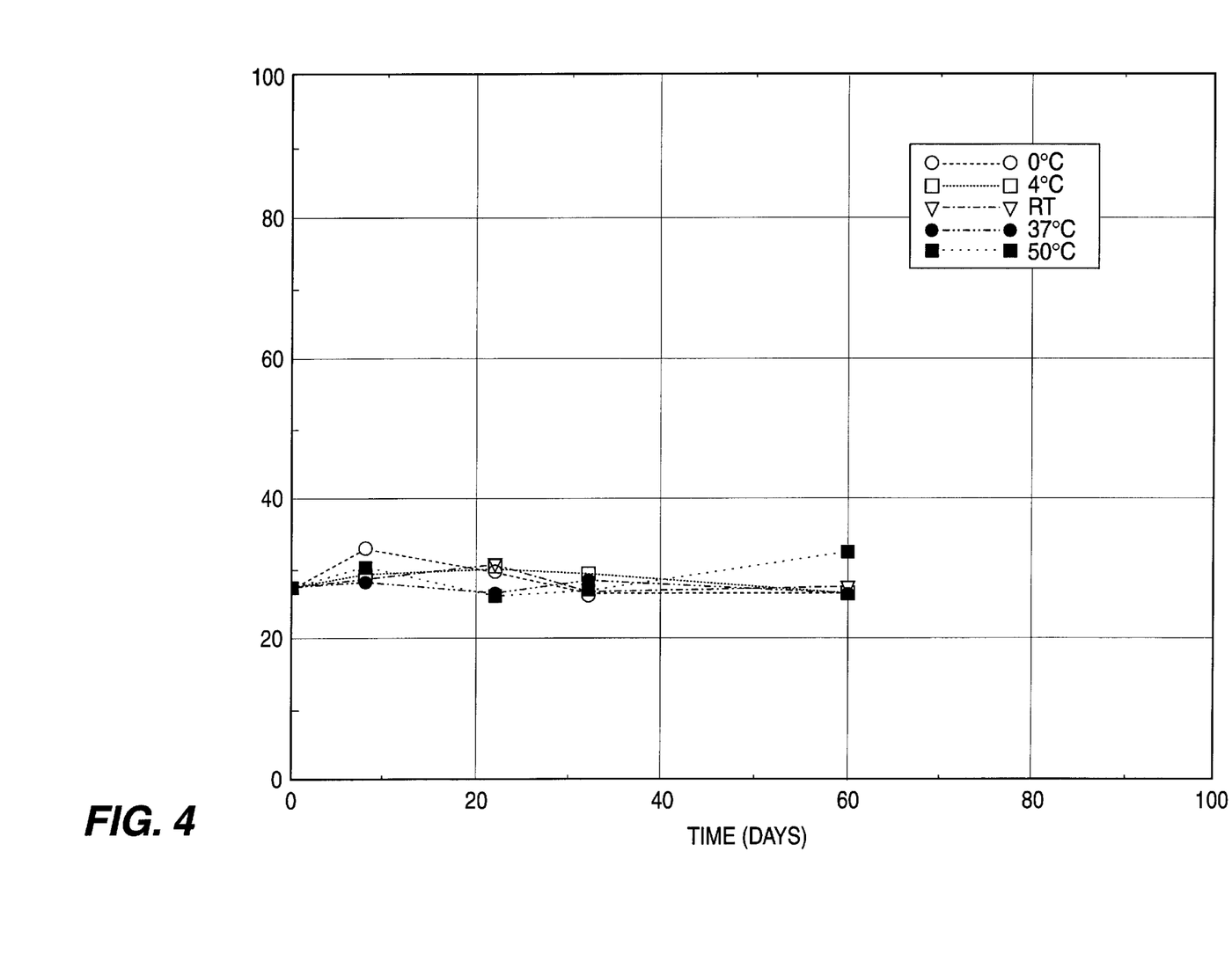

In FIG. 4, the concentration of N-(3-methylbenzyl)-diglycolic acid, monoamide was 0.750 ppm which is equivalent to approximately 3.00 ppm.

At each concentration of the N-(3-methylbenzyl)-diglycolic acid, monoamide, the immunoassay was performed at various temperatures denoted in the Figure summarizing the results. The results show that the N-(3-methylbenzyl)-diglycolic acid, monoamide was essentially stable over a period of 60 days, the longest times tested.

Example 5

Results with acenaphthene, anthracene, and phenanthracine, 2,4-D, and naphthalene Acenapthene, because of its boiling point (279° C., Merck Index), is known to be stable as regards volatilization. It is also immunoreactive (see Table 2) with an immunoreactivity (immunoreactivity being considered to be inversely proportional to their 50% $B/B_0$) that is 1.80/6.20 that of m-xylene. Therefore, acenaphthene is concluded to be a stable standard.

Figure 5:
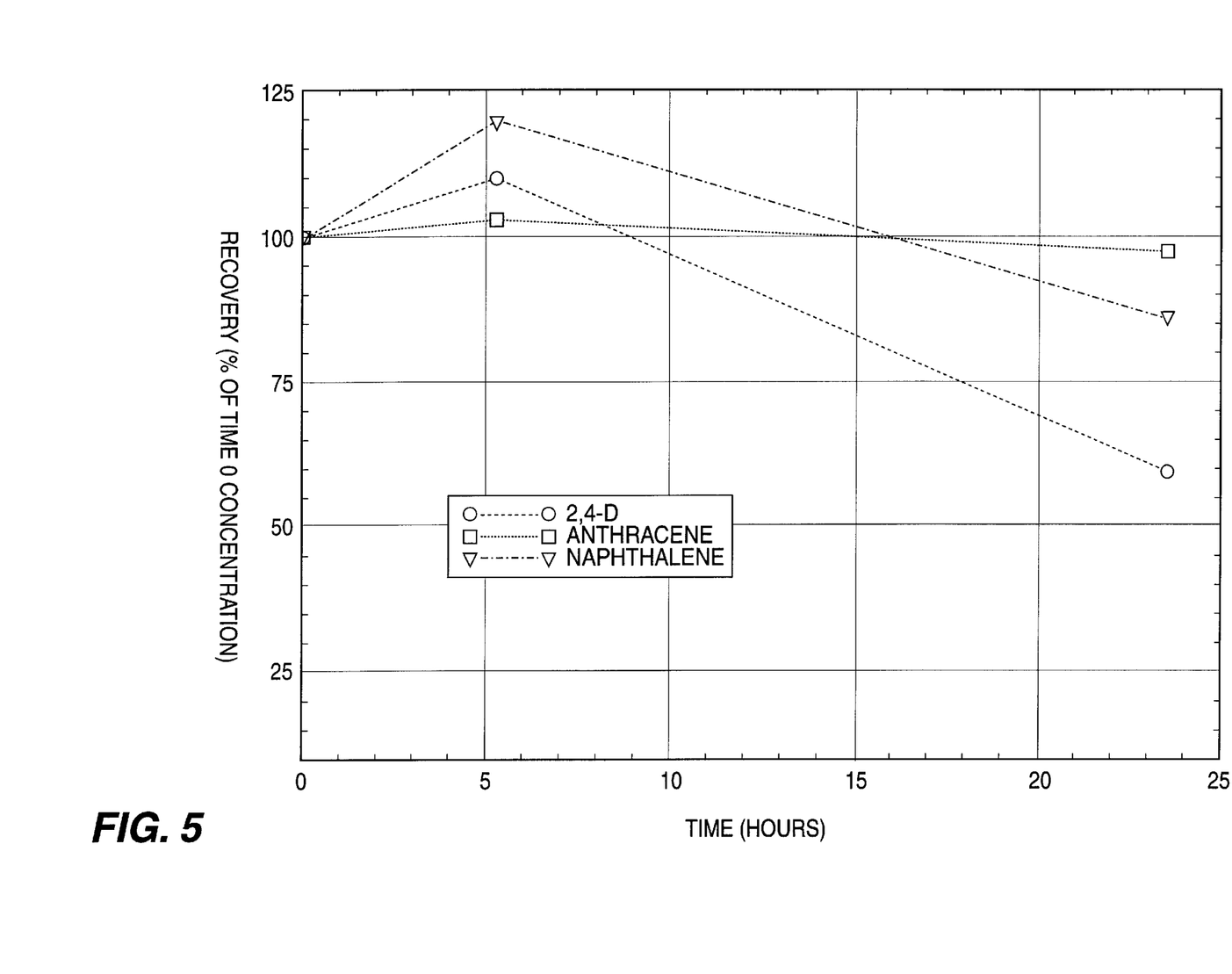
FIG. 5 shows the effect of storage on the concentration of various compounds.

Additionally, preparations of anthracene (20 ppm), naphthalene (0.75 ppm), and 2,4-D (10 ppm), were tested for their immunoreactivity using the conditions of using the conditions described in Example 1. The results are shown in FIG. 5.

Figure 6:
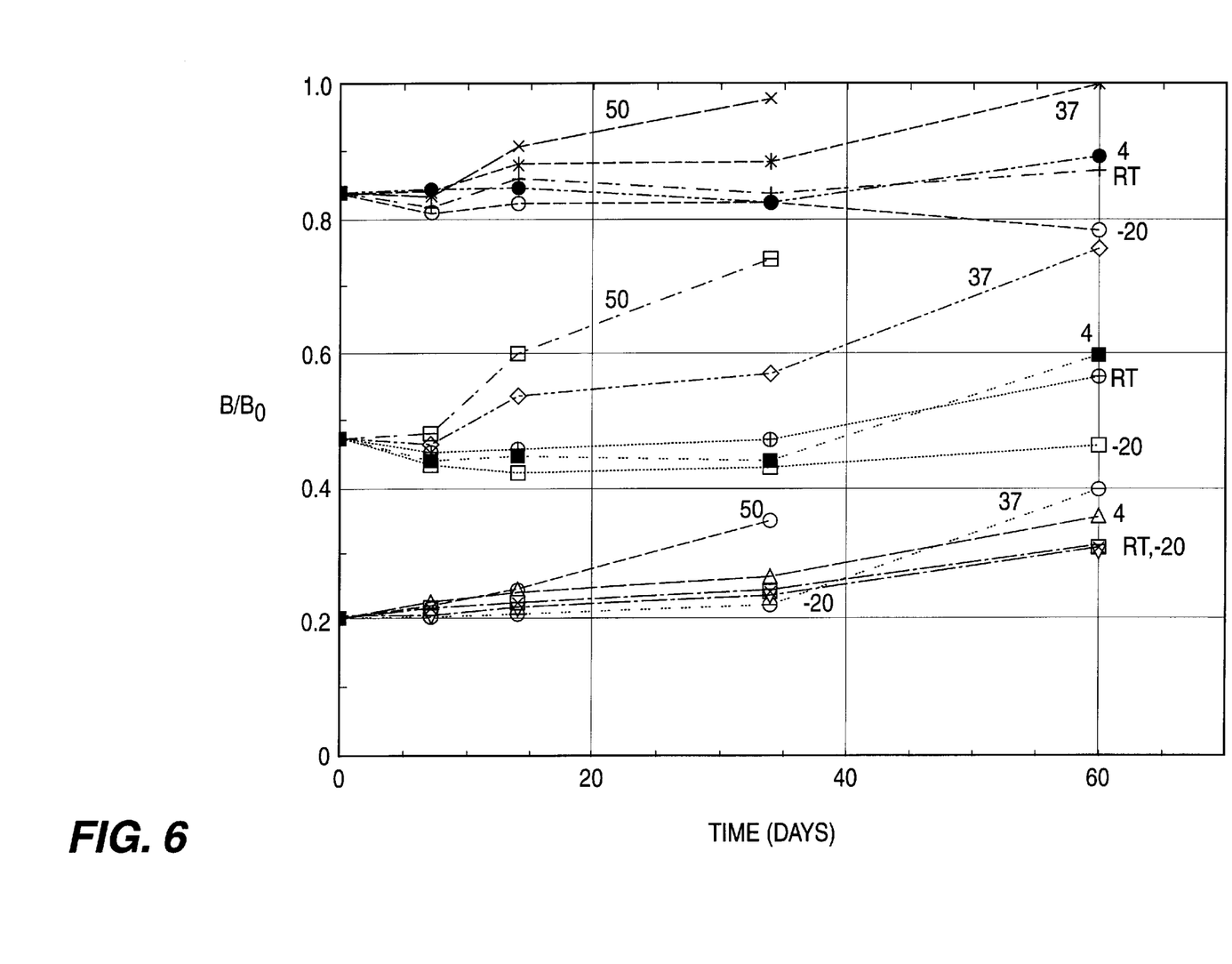
FIG. 6 shows the effect of storage on the concentration of anthracene.
Figure 7:
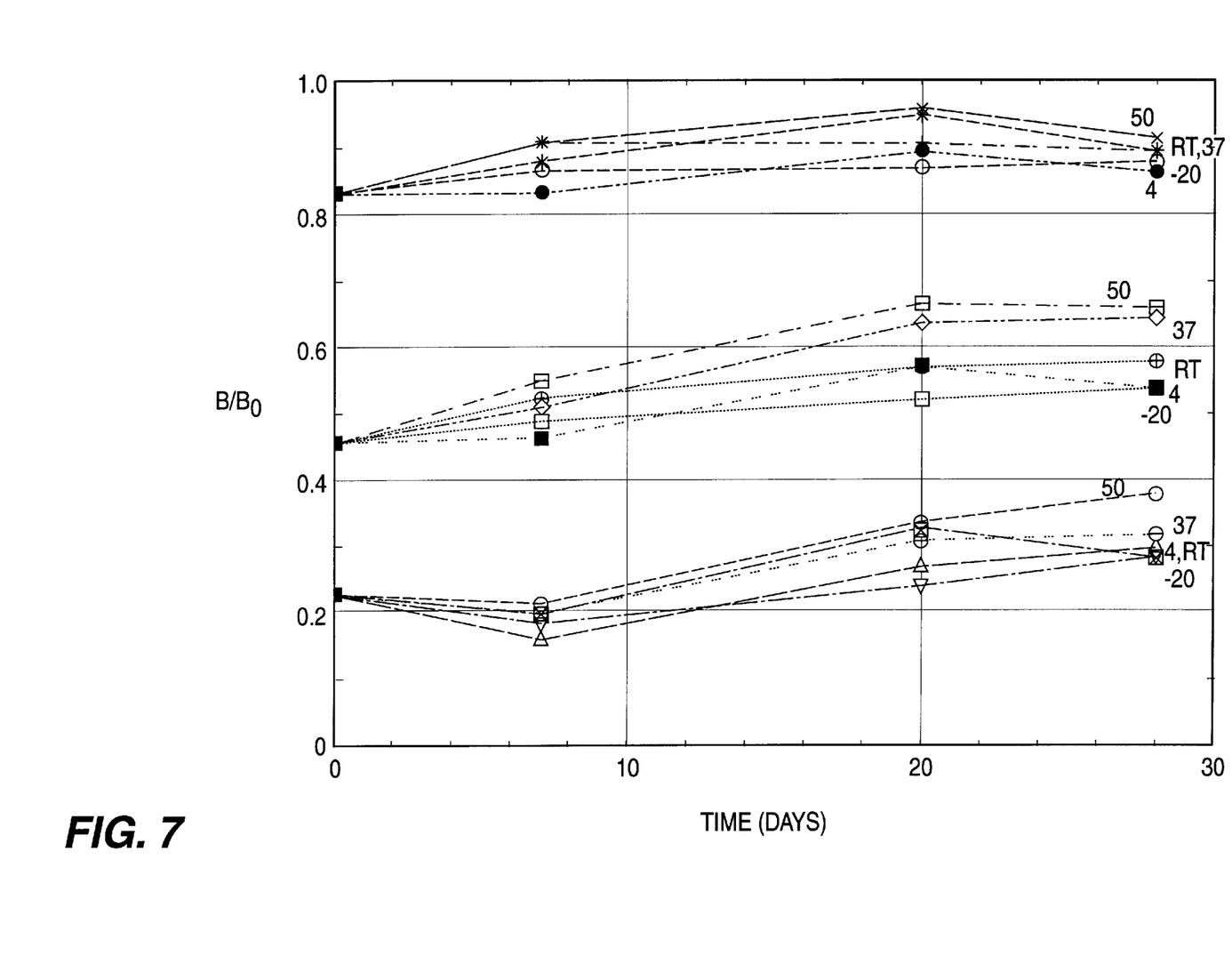
FIG. 7 shows the effect of storage on the concentration of phenanthrene.

Additional experiments were done using volumes of 2.5 ml in 3.5 ml vials and an antibody preparation reactive with anthracene and phenanthrene, the antibodies not made with the immunogen described herein and although much less suited for purposes of the present inventions than that made from the described immunogen, were adequate for obtaining the stability curves. (The results were considered to essentially reflect what would have occurred if the storage was done with 2 ml of solution in a 3 ml vial.) Anthracene was tested at concentrations of 1 ppb (upper set of curves in FIG. 6), 10 ppb (middle set of curves in FIG. 6) and 100 ppb (lower set of curves in FIG. 6) in TBS pH 7.0 at the specified temperatures in FIG. 6. Phenanthrene was tested at concentrations of 1 ppb (upper set of curves in FIG. 7), 10 ppb (middle set of curves in FIG. 7) and 100 ppb (lower set of curves in FIG. 7) in TBS at pH 7.0 at the specified temperatures in FIG. 7. TBS is 25 mM Tris, 150 mM NaCl, 1 mM EDTA, 0.1% BSA, with 15 ppm active Proclin, pH 7.0.

The results indicated that:
(1) anthracene is very stable (meets the 14-day test), particularly if used within about 5 to 10 days.
(2) Phenanthrene is very stable (meets the 14-day test), particularly if used within about 5 days.
(3) 2,4-D is more stable than m-xylene but less stable than anthracene.
(4) Naphthalene is not sufficiently stable to be considered a preferred compound, although it is more stable than m-xylene.

Example 6

Calculation of 50% $B/B_0$

Figure 8:
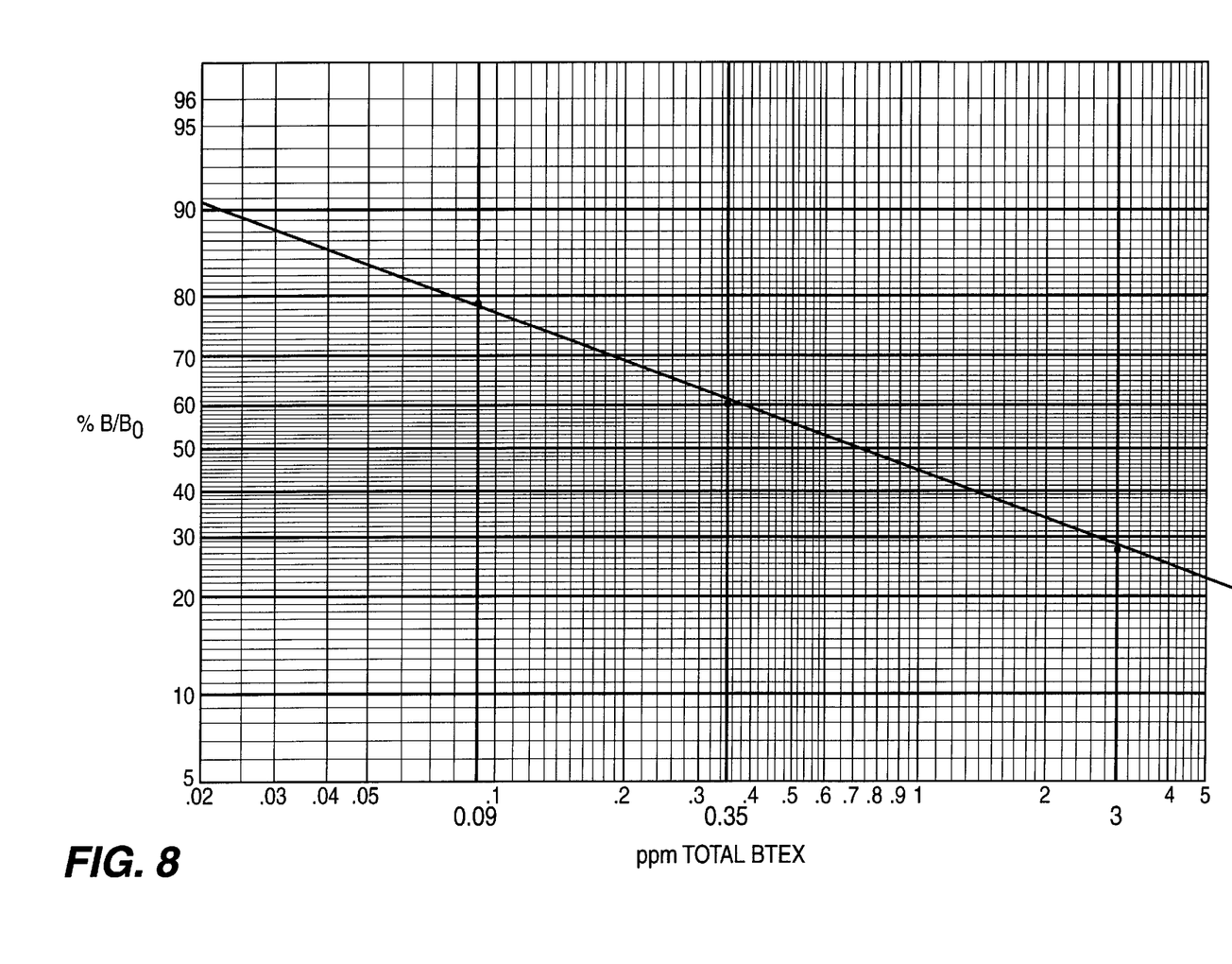
FIG. 8 Example of a standard curve.

An example of a curve plotting the % $B/B_0$ for a standard on vertical logit (Y) axs versus the corresponding analyte concentration on a horizontal algorithmic (X) axis is shown in FIG. 8. The curve is for Total BTEX. The value for 50% $B/B_0$ is 0.7 ppm.

What is claimed is:

1. An Immunoassay process for detecting an analyte, which process comprises the steps of:
   (1) reacting a sample with an antibody preparation, said sample comprising an amount of analyte, said antibody reactive against said analyte,
   (2) reacting a known amount of standard with an antibody preparation of the same specificity as that used in step (1),
   (3) quantitating the amount of the antibody preparation that reacted with the sample in step (1),
   (4) quantitating the amount of antibody preparation that reacted with the standard in step (2), and
   (5) utilizing the amounts quantitated in step (3) and (4) and the known amount in step (2) to calculate the amount or an upper limit to the amount of analyte present in the sample used in step (1),
   wherein the assay detects benzene as an analyte and wherein the standard is stored in water and is a compound that displays at least 70 per cent nonvolatilization in water after 14 days storage at 25° C. when stored in a closed 3 ml vial as a 2 ml aqueous solution and wherein the standard comprises a benzene ring.

2. An immunoassay of claim 1 which comprises reacting an antibody preparation with the analyte, said antibody preparation prepared by using an immunogen that comprises xylene linked via one of its methyl groups to a carrier.

3. An immunoassay of claim 2 wherein the immunogen comprises m-xylene linked via one of its methyl groups to a carrier.

4. An immunoassay of claim 1 wherein the standard has a boiling point greater than 200° C.

5. An immunoassay of claim 1 wherein the standard is a substantially pure preparation of a single compound.

6. A process of claim 1 wherein the standard is a mixture of one or more substantially pure compounds, said mixture constructed by mixing together portions of pure preparation of said compounds.

7. A process of claim 1 wherein the standard has a molecular weight greater than 130.

8. An immunoassay of claim 1 wherein the analyte is part of a mixture selected from the group, gasoline, diesel fuel, jet fuel, and kerosene.

9. A kit for performing the immunoassay of claim 1, said kit comprising a standard stored in water, an analyte reactive antibody, and instructions for performing the immunoassay, wherein the analyte is benzene, and wherein the standard is a compound that comprises a benzene ring and displays at least 70 per cent nonvolatilization in water after 14 days storage at 25° C. when stored in a closed 3 ml vial as a 2 ml aqueous solution.

10. An immunoassay of claim 1 wherein the assay detects as analyte, benzene, toluene, ethylbenzene, and xylene.

11. An immunoassay of claim 1 wherein the standard is a compound in which a single benzene ring is the only ring structure.

12. An immunoassay of claim 10 wherein the standard is a compound in which a single benzene ring is the only ring structure.

13. A process of claim 11 wherein the standard has a molecular weight greater than 130.

14. A process of claim 12 wherein the standard has a molecular weight greater than 130.

15. An assay of claim 1 wherein the standard is selected from the group, anthracene, phenanthrene, 2,4-D, and N-(3-methylbenzyl)-diglycolic acid, monoamide.

16. An assay of claim 15 wherein the standard is N-(3-methylbenzyl)-diglycolic acid, monoamide.

17. A kit for detecting an analyte, said kit comprising N-(3-methylbenzyl)-diglycolic acid, monamide in water, said kit further comprising an antibody that reacts with an analyte that has a boiling point less than 200° C., said analyte comprising a benzene ring, which benzene ring may be part of a multi-ring structure, which benzene ring may be substituted at one or more of its six carbon atoms such that the substituent at one atom need not be the same as the substituent at another atom, such that not more than one substituent on said benzene ring is other than I, Cl, Br, OH,—$CH_3$, or —$NO_2$, wherein any substituent on said benzene ring that is not I, Cl, Br, OH, —$CH_3$, or $NO_2$, has a backbone chain that does not have more than six atoms, said kit further comprising instructions for using the antibody and standard to detect said analyte.

* * * * *